(12) United States Patent
Levinsohn

(10) Patent No.: US 12,207,812 B2
(45) Date of Patent: Jan. 28, 2025

(54) DISPOSABLE INSTRUMENT NOSEPIECES FOR REPAIRING SOFT TISSUE TO BONE COUPLING

(71) Applicant: ORTHONOBLE INC., Del Mar, CA (US)

(72) Inventor: David Levinsohn, Del Mar, CA (US)

(*) Notice: Subject to any disclaimer, the term of this patent is extended or adjusted under 35 U.S.C. 154(b) by 1282 days.

(21) Appl. No.: 16/303,055

(22) PCT Filed: May 17, 2017

(86) PCT No.: PCT/US2017/033195
§ 371 (c)(1),
(2) Date: Nov. 19, 2018

(87) PCT Pub. No.: WO2017/201216
PCT Pub. Date: Nov. 23, 2017

(65) Prior Publication Data
US 2023/0047099 A1    Feb. 16, 2023

Related U.S. Application Data

(60) Provisional application No. 62/338,336, filed on May 18, 2016.

(51) Int. Cl.
*A61B 17/04*    (2006.01)
*A61B 17/00*    (2006.01)

(52) U.S. Cl.
CPC .. *A61B 17/0401* (2013.01); *A61B 2017/0046* (2013.01); *A61B 2017/0409* (2013.01);
(Continued)

(58) Field of Classification Search
CPC ........ A61B 17/0401; A61B 2017/0414; A61B 2017/00473; A61B 2017/00464;
(Continued)

(56) References Cited

U.S. PATENT DOCUMENTS

| | | | | |
|---|---|---|---|---|
| 4,258,722 A | * | 3/1981 | Sessions | A61B 10/025 600/566 |
| 5,050,420 A | * | 9/1991 | Liu | B25B 27/0007 72/391.8 |

(Continued)

OTHER PUBLICATIONS

PCT/US2017/033195, "International Search Report", Aug. 28, 2017, p. 1-2.
(Continued)

*Primary Examiner* — Dianne Dornbusch

(57) ABSTRACT

In one embodiment, a suture anchor installation system for orthopedic surgery is disclosed including a reusable or disposable handle, and one or more reusable or disposable screw-on tool nosepieces for orthopedic surgery that are configured to be coupled to the handle. The one or more reusable or disposable screw-on tool nosepieces include an awl, a tap, a suture anchor install tool, and a suture anchor adjustment tool for orthopedic surgery. The nosepieces may alternatively press-on or snap-on with a barb/groove configuration or rectangular driver/ball/socket universal joint configuration with an engineering fit such as a running, sliding, or slip fit, a locational or transition fit, a force fit, a friction fit, or an interference fit.

8 Claims, 7 Drawing Sheets

(52) U.S. Cl.
CPC .............. *A61B 2017/0414* (2013.01); *A61B 2017/0416* (2013.01)

(58) Field of Classification Search
CPC .... A61B 2017/0046; A61B 2017/0458; A61B 2017/0445; A61B 2017/0416; A61B 2017/0411; A61B 2017/0409
See application file for complete search history.

(56) References Cited

U.S. PATENT DOCUMENTS

| | | | | |
|---|---|---|---|---|
| 5,217,486 | A * | 6/1993 | Rice | A61B 17/0401 606/328 |
| 5,257,973 | A * | 11/1993 | Villasuso | A61B 17/34 128/912 |
| 5,258,016 | A | 11/1993 | DiPoto et al. | |
| 5,730,747 | A | 3/1998 | Ek et al. | |
| 5,814,051 | A | 9/1998 | Wenstrom, Jr. | |
| 5,993,459 | A * | 11/1999 | Larsen | A61B 17/0469 606/104 |
| 6,106,539 | A * | 8/2000 | Fortier | A61B 17/3417 604/164.06 |
| 6,162,234 | A | 12/2000 | Freedland et al. | |
| 6,244,141 | B1 * | 6/2001 | Han | B25B 23/10 81/453 |
| 6,258,091 | B1 * | 7/2001 | Sevrain | A61B 17/688 606/301 |
| 7,637,896 | B2 * | 12/2009 | Voegele | A61B 17/3417 604/264 |
| 8,460,309 | B2 | 6/2013 | Howe | |
| 8,460,340 | B2 * | 6/2013 | Sojka | A61B 17/0485 606/232 |
| 9,572,563 | B2 * | 2/2017 | Berelsman | A61B 17/0401 |
| 2004/0030410 | A1 * | 2/2004 | Wagman | A61F 2/78 623/32 |
| 2006/0293702 | A1 * | 12/2006 | Buser | A61B 17/3496 606/185 |
| 2008/0004659 | A1 * | 1/2008 | Burkhart | A61B 17/0401 606/232 |
| 2008/0033460 | A1 | 2/2008 | Ziniti et al. | |
| 2009/0192546 | A1 * | 7/2009 | Schmieding | A61B 17/0401 606/232 |
| 2010/0305576 | A1 | 12/2010 | Ferguson et al. | |
| 2011/0270308 | A1 | 11/2011 | Kilburn-Peterson et al. | |
| 2013/0079817 | A1 * | 3/2013 | Sengun | A61B 17/0401 606/232 |
| 2014/0277128 | A1 | 9/2014 | Moore et al. | |
| 2017/0156726 | A1 * | 6/2017 | Bouduban | A61B 17/0401 |

OTHER PUBLICATIONS

PCT/US2017/003195. "Written Opinion of the International Searching Authority", Aug. 28, 2017, pp. 1-6.

* cited by examiner

DISPOSABLE INSTRUMENT NOSEPIECES FOR REPAIRING SOFT TISSUE TO BONE COUPLING

CROSS REFERENCE TO RELATED APPLICATIONS

This United States (U.S.) patent application claims the benefit of U.S. Provisional Patent Application No. 62/338,336 titled DISPOSABLE INSTRUMENT NOSEPIECES FOR REPAIRING SOFT TISSUE TO BONE COUPLING filed on May 18, 2016 by inventor David Levinsohn.

FIELD

The embodiments of the invention relate to tools for orthopedic surgery to repair a coupling between soft tissue and bone.

BACKGROUND

Soft tissue injures at bone attachments sites are a major cause of musculoskeletal problems for which patients seek care and subsequently require surgery. For example, the rotator cuff is the anatomical term given to a group of muscles and their tendons that act to move and stabilize the shoulder, which can experience tearing.

The miniaturization of suture anchors is an important development that has allowed use of suture anchors for improved techniques to repair the connection of soft tissue to bone in certain situations. Examples are arthroscopic hip and shoulder labral repair, arthroscopic knee meniscus repair, and open finger and toe tendon repair.

However, the installation of suture anchors into bone during orthopedic surgery takes some time and effort. A number of expensive sterilized instruments or tools that are used during orthopedic surgery are simply single use and disposable resulting in significant waste and cost. Often times a sterilized instrument that has been re-used over a few years doesn't perform optimally because it has some damage. The damage is often insufficiently observable during inspection to warrant tossing it away. Time is sometimes lost in surgery seeking another instrument or tool that is effective. If orthopedic surgery can be more efficient, the patient spends less time in surgery and surgical costs may be reduced including decreased valuable limited storage space for inventory and decreased volume of instruments to clean and instrument carts to prepare.

Accordingly, there remains a need for improved devices and methods to secure soft tissue to bone.

SUMMARY

The embodiments of the invention are summarized by the claims that follow below.

DETAILED DESCRIPTION

Figure 1A:
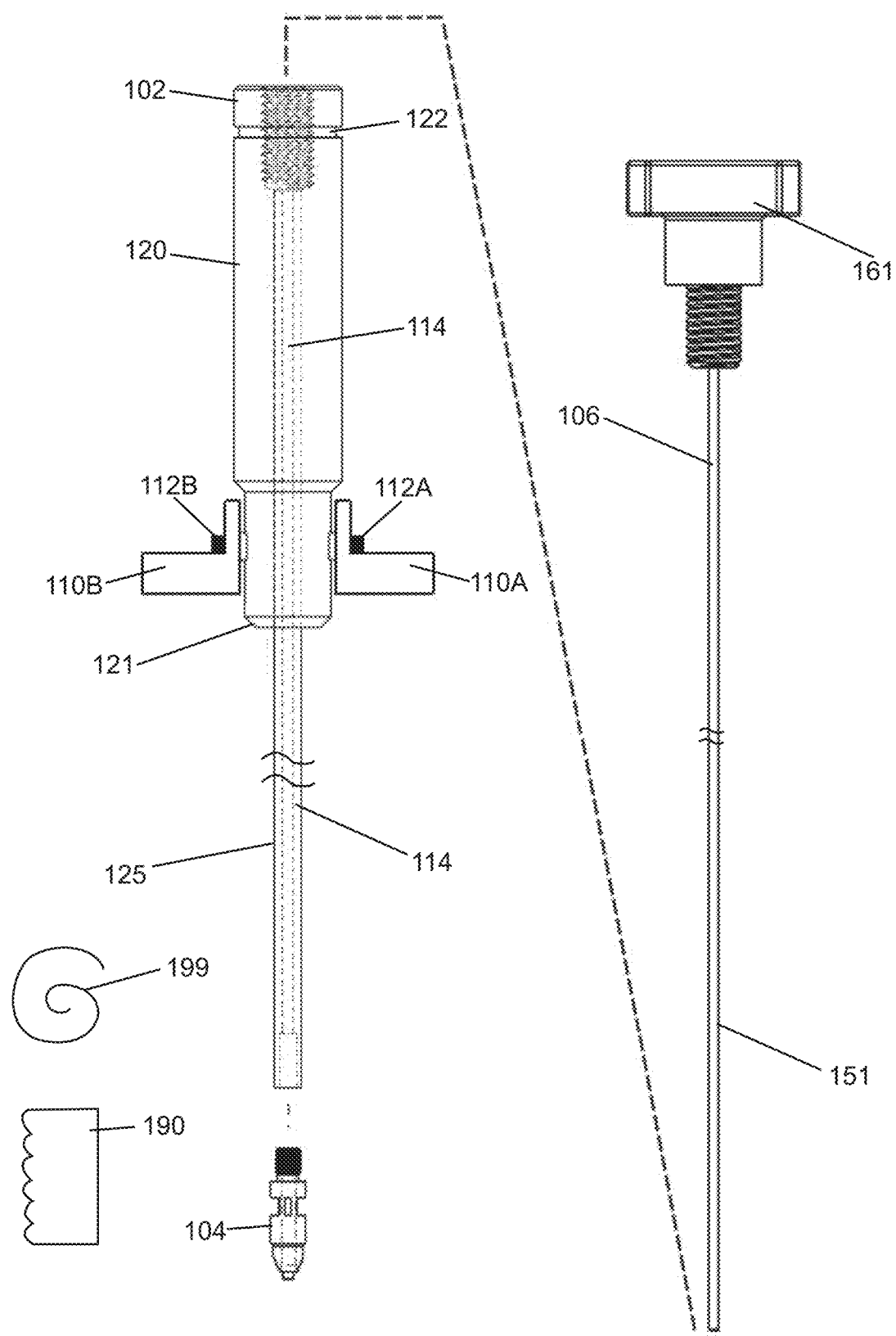
FIG. 1A illustrates a suture anchor installation system including an installation handle, a screw-on disposable tool nosepiece, an eyelet rod, and one or more sterile bags.

In the following detailed description of the embodiments, numerous specific details are set forth in order to provide a thorough understanding of the embodiments. However, it will be obvious to one skilled in the art that the embodiment may be utilized without these specific details. In other instances well known surgical methods, procedures and related medical components have not been described in detail so as not to unnecessarily obscure aspects of the embodiment.

As used herein, the term "proximal" or "proximate" refers to the relative position that is closest to the center of the body when the suture anchor device is implanted.

As used herein, the term "distal" refers to the relative position that is farthest from the center of the body when the suture anchor device is implanted or anchor installation tool is used.

As used herein, the term "longitudinal" refers to the direction that is parallel to the longitudinal axis of the suture anchor device or anchor installation tool.

As used herein, the term "complementary engagement structures" refer to structural features that position the eyelet pin of the suture anchor in relation to the outer body in a manner such that the eyelet pin can be released when sufficient force is applied to the eyelet pin or outer body.

As used herein, the term subject, body, or patient refers to an animal having an endoskeleton such as a human being.

A device described herein is hardware, such as an anchor installation tool, a single use suture anchor, suture thread, or a combination of hardware including one or more of the anchor installation tool, the single use suture anchor, and the suture thread.

INTRODUCTION

Disposable surgical instruments can represent significant waste in the operating room. Waste can drive up costs of an orthopedic surgery and decrease efficiency and quality of care.

Some commonly used surgical instruments in orthopedic surgery, namely awls or punches, and taps are often wasted after a single use. Different types and sizes of suture anchors may require different types and sizes of surgical instruments. Suture anchor installation systems have many awls and taps to install a family type of suture anchors. The surgical instruments are generally not sold with the suture anchor. Moreover, these manual orthopedic surgical instruments are not set for re-use.

When re-used, these instruments are sterilized individually. The type of surgical instruments are poorly identified by labeling on the device and the handwritten labeling on the surface of an in-house sterile package. Over time, these type of instruments become damaged and do not perform optimally for years before being replaced.

To combat waste, a universal instrument handle or a small series of universal instrument handles, can be adapted for use with all of the different types of suture anchors, including knotless and regular suture anchors, hybrid suture anchors comprised of graft material such as a collagen mesh and sutures and tapes. The same instrument handle or a small series of instrument handles, can be adapted as the various installation tools to allow a suture anchor be deployed into bone, including adjustment tools, removal tools for suture anchors, suture cutting instrument and suture passing and shuttling tools.

In this manner of the universal instrument handle can be reused to reduce waste, decrease costs, and decrease inventory size of the manual surgical instruments used in orthopedic surgery.

A suture anchor installation system for soft tissue repair to bone is disclosed. The suture anchor installation system includes an insertion instrument handle that can be configured for a variety of purposes including; applying a knotted suture anchor or knotless suture anchor or all suture anchor into bone or hybrid suture anchor comprised of material such as a collagen mesh with sutures and or suture tape, use as a tap, as a awl, use as an adjustment tool to adjust the tension of a soft tissue repair or adjust the depth of a suture anchor, use as a tool to remove a suture anchor, use as a suture passing device, use as a suture cutter, use as a suture grabber and use as a suture shuttling device.

In one embodiment the handle has a shaft with a distal tip configured to accept an appropriate nosepiece or screw-on tip including one or more of the following functions: a nosepiece for a knotted suture anchor, a nosepiece for a knotless suture anchor, a nosepiece for an all suture suture anchor, a nosepiece for a hybrid suture anchor, and a nosepiece that can be used for one or more types of suture anchors, a nosepiece for use as a tap, a nosepiece for use as an awl, a nosepiece for use as an adjustment tool to adjust the tension of a soft tissue repair or adjust the depth of a suture anchor, a nosepiece for use as a tool to remove a suture anchor, a nosepiece for use as a suture passing device, a nosepiece for use as a suture cutter, a nosepiece for use as a suture grabber and a nosepiece for use as a suture shuttling device.

The suture anchor installation system may further include sterile packages of suture anchor implants for single use that are configured for specific or custom purposes. The sterile packaging, may include one of more the following: one or more instrument handles, one or more of the following nosepieces: taps, awls, suture anchors including knotless and knotted suture anchors, all suture suture anchors, hybrid suture anchors comprised of material such as a collagen mesh and sutures and tapes, tools to allow engagement of the instrument into or onto a suture anchor for the deployment into bone, adjustment tools, removal tools for suture anchors, suture cutting tool, suture passing tool, suture grabbing tool and shuttling tools.

It is understood that the purpose of the system described is not necessarily exclusive to the embodiments mentioned but can be adapted to one or more instrument handles and tools that facilitate soft tissue repair to bone. In some embodiments, the shaft of the instrument handle is configured to be inserted into a cannula for its length, allowing sutures to placed within the lumen of the handle.

In some embodiments the instrument handle includes cleats to allow tensioning of suture threads that are wrapped around the cleat. In some embodiments the instrument handle and its shaft are configured to receive a central eyelet complex impaction rod including a rod coupled to a knob with threads proximally on the rod that correspond to threads in the inner wall of the shaft of the instrument. In some embodiments, the instrument handle would include a mechanism to effect suture capture within a suture anchor. In some embodiments, a surgeon, or an assistant to the surgeon, would place sutures into a suture anchor and retrieve these from the cannulated shaft of the anchor installation instrument with a long suture passer.

Sterile kits are disclosed with a sterile bag including one or more instrument handles and one or more of: knotted suture anchor or knotless suture anchor; a hybrid suture anchor comprised of material such as a collagen mesh with sutures and or suture tape, sutures, suture tape; one or more screw-on nosepieces with functions including but not to the following uses: as a tap, as an awl, as an adjustment tool to adjust the tension of a repair or adjust the depth of the implant, as a tool to remove the implant, as a suture passing device, as a suture cutter, as a suture grabber and as a suture shuttling device.

In some embodiments, an instrument cart is used to support the re-usable instruments or tools including one or more instrument handles; one or more various types of nosepieces that couple to the shaft of the instrument handle including a tap, an awl, an adjustment tool to adjust the tension of a repair or adjust the depth of suture anchor, a removal tool to remove the implant, a tool to be sued as a suture passing device, a tool to be used as a suture cutter, a tool to be used as a suture grabber, and a tool to be used as a suture shuttling device.

Suture Anchor Installation Tool and System

Referring now to FIG. 1A, a suture anchor installation system 100 is shown. The suture anchor installation system 100 includes an installation tool comprising an installation handle 102 with a hollow shaft 125 and one or more screw-on disposable tool nosepieces 104. The suture anchor installation system may further include an eyelet complex impaction rod 106. The suture anchor installation system may further include one or more suture threads 199 (each having a left end and a right end), one or more suture anchors 350, and one or more sterile bags 190.

Different types of screw-on disposable tool nosepieces 104 may be stored in the sterile bags. The installation handle 102 with a hollow shaft 125 may be stored in a separate sterile bag. The eyelet complex impaction rod 106 may be stored in a different sterile bag. Suture thread and different size/types of anchors may be stored in a sterile bag prior to a surgery. As needed, the one or more sterile bags may be opened to gain access to the components of the suture anchor installation system.

The installation handle 102 of the anchor installation tool includes a metal (smooth or knurled) or molded plastic circular cylindrical handle body 120 and a parallel sidewall extrusion 121 coupled together. The circular cylindrical handle body 120 of the installation handle 102 may include a circular groove 122 to receive excess suture thread. The handle body 120 may have a knurled gripping surface to provide a firm griping surface to a gloved hand of a surgeon to avoid slips when using the installation tool.

Left and right side cleats 110A-110B may be mounted to respective sides of the parallel sidewall extrusion 121 by respective fasteners 112A-112B.

One end of the hollow shaft 125 couples to the sidewall extrusion 121 of the handle 102. The end of the hollow shaft may be fused into the end of the sidewall extrusion 121. The end of the hollow shaft may have external threads and may be threaded into the end of the sidewall extrusion 121 having internal threads. In any case, the hollow shaft 125 couples to the installation handle 102.

A cylindrical channel 114 extends along the longitudinal axis of the installation handle 102. A cylindrical channel 114 similarly extends along the longitudinal axis of the hollow shaft 125. The eyelet complex impaction rod 106 includes a rod 151 and a cylindrical handle 161. An end of the eyelet complex impaction rod 106 may be inserted into the cylindrical channel 114 and extend through the handle and into the cylindrical channel 114 of the shaft 125.

The installation handle may be reusable or disposable. The one or more screw-on tool nosepieces 104 may be for one time use and disposable or they may be reusable.

Screw-on Tool Nosepieces

Figure 1B:
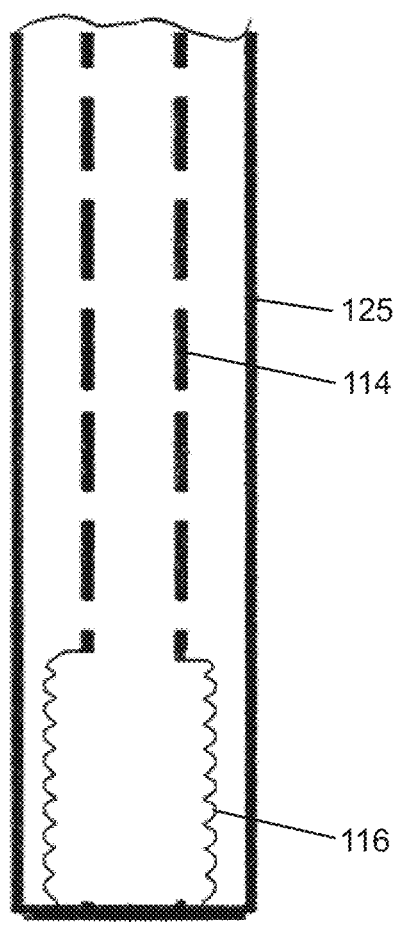
FIG. 1B illustrates a magnified view of the screw-on disposable tool nosepiece that may be coupled to the end of a shaft of the installation handle.
Figure 1B:
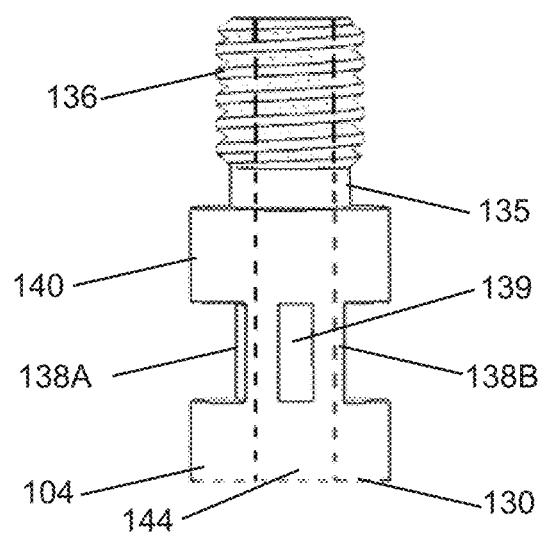

Referring now to FIG. 1B, a magnified side view of the screw-on tool nosepiece 104 is shown. The screw-on tool nosepiece 104 includes a threaded shaft 135 with outer (male) threads 136 coupled to the proximal end of body 140 of the nosepiece. The threaded shaft 135 includes outer threads 136. The body 140 has a distal end 130 to which another structure is coupled to customize the type of nosepiece that is formed.

The end of the hollow shaft 125 coupled to the installation handle includes an inside threaded opening 116 with inner (female) threads that receives the outer (male) threads 136 of the shaft of the nosepiece 104. In one embodiment, the inside threaded opening 116 and the outer threads 136 are right handed threads so that when the handle is turned clockwise, the nosepiece 104 is threaded into the threaded opening of the shaft. In another embodiment, the threads may be left-handed threads. In yet another embodiment, the outer threads may be at the end of the shaft 125 while the inner threads are in the nosepiece 104.

While the nosepiece is described as being a screw-on nosepiece with a threaded joint, other methods/joints (e.g., press-on or snap-on) for attaching the removable nosepiece to the shaft of the universal handle may be used, such as a barb/groove configuration or a rectangular driver/ball/socket joint configuration with an engineering fit (e.g., a running, sliding, or slip fit, a locational or transition fit, a force fit, a friction fit, or an interference fit).

The nosepiece 104 includes opposing jaw receptacles 138A-138B to receive the jaws of a wrench to tighten the nosepiece into and against the end of shaft 125. The nosepiece further includes a rectangular recess 139 to receive an alternate wrench to tighten the nosepiece 104 into and against the end of shaft 125.

In some embodiments, the nosepiece includes a cylindrical opening 144 along the longitudinal axis of its body 140. The cylindrical opening 144 mates with the cylindrical opening 114 in the shaft 125 and handle to receive a supplemental tool, such as the rod of the eyelet complex impaction rod shown in FIG. 1A.

Figure 2A:
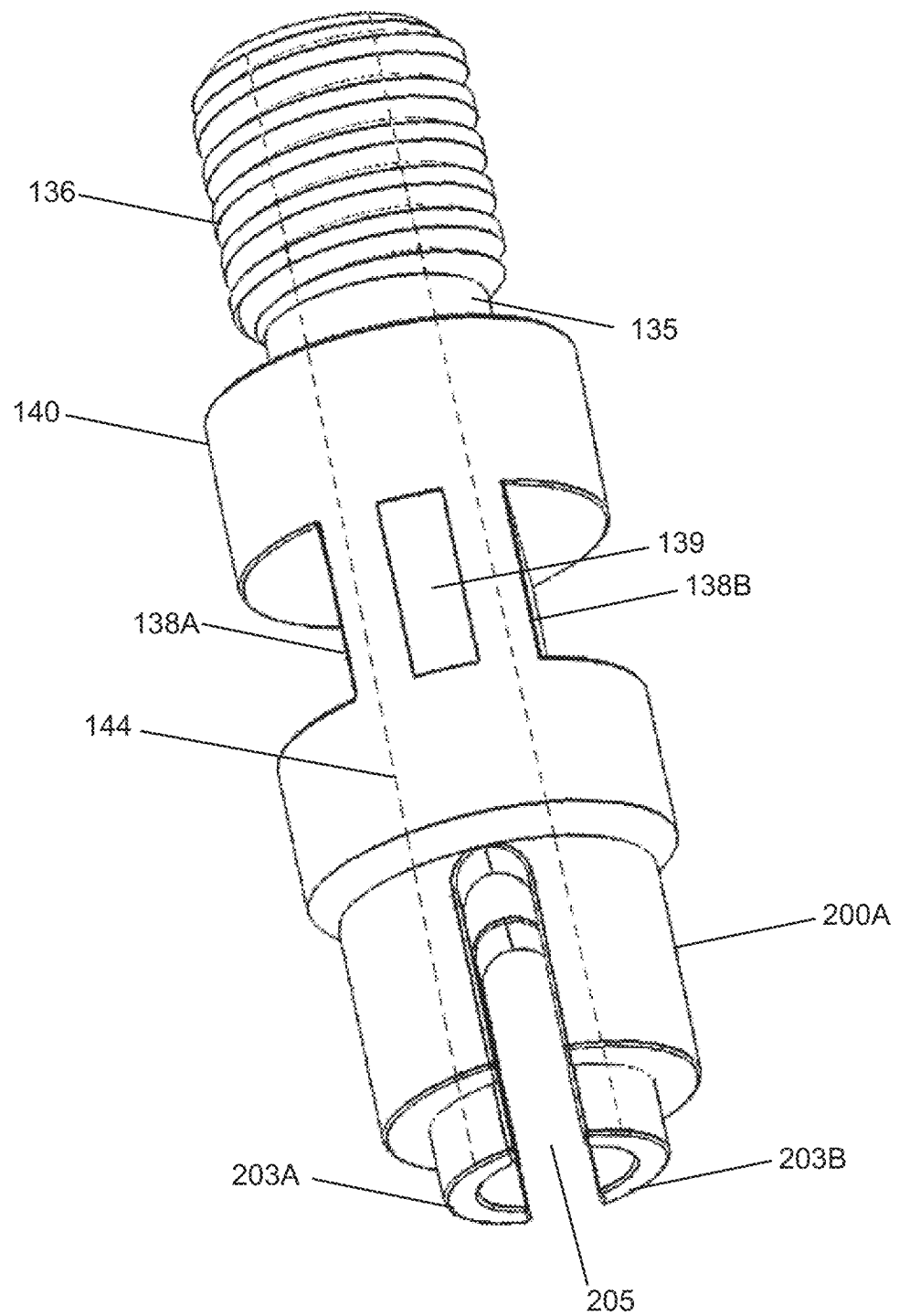
FIG. 2A illustrates a perspective view of a first embodiment of the screw-on disposable tool nosepiece.
Figure 2B:
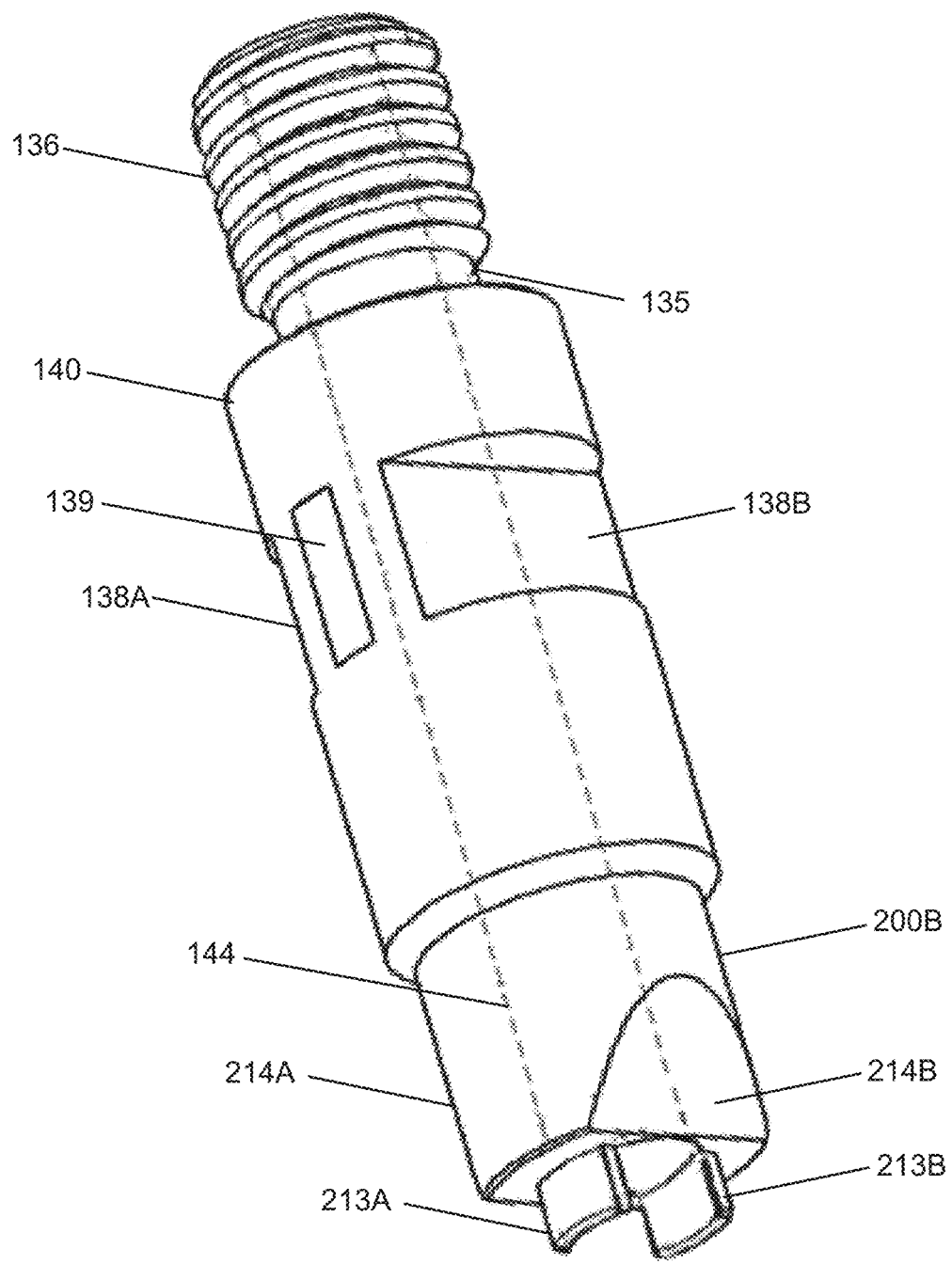
FIG. 2B illustrates a perspective view of a second embodiment of the screw-on disposable tool nosepiece.
Figure 2C:
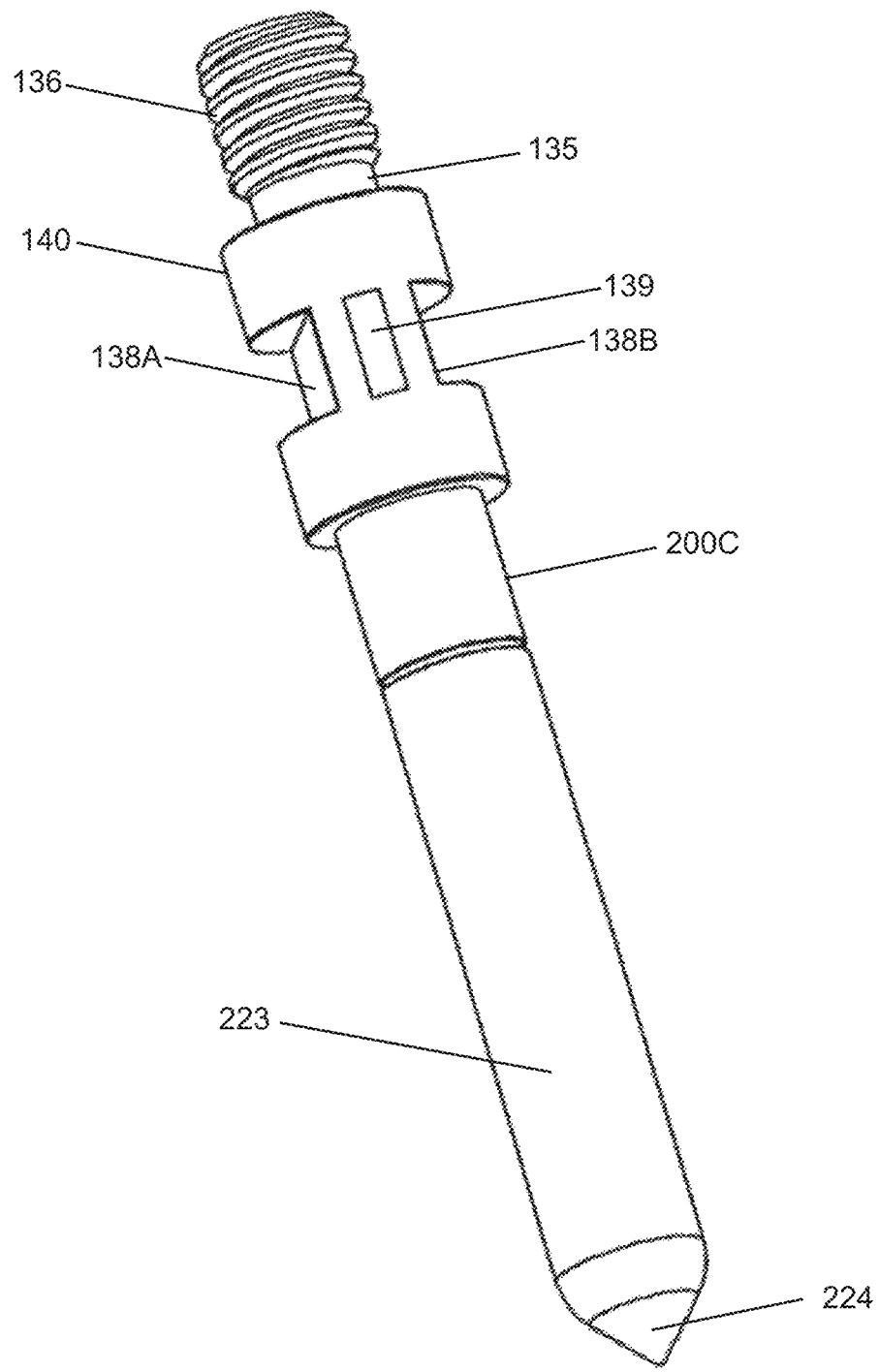
FIG. 2C illustrates a perspective view of a third embodiment of the screw-on disposable tool nosepiece.

FIGS. 2A-2C illustrate various embodiments 104A-104C of the generic screw-on disposable tool nosepiece 104 shown in FIGS. 1A-1B. Each of the various embodiments 104A-104C shown in FIGS. 2A-2C include one or more elements of the generic screw-on disposable tool nosepiece 104. For brevity, the description of those elements are incorporated herein by reference.

Referring now to FIG. 2A, a perspective view of a screw-on disposable anchor install tool nosepiece 104A is shown. The nosepiece 104A includes the threaded shaft 135 coupled to one end of its body 140. The body 140 includes the opposing jaw receptacles 138A-138B and the rectangular recess 139 to receive various types of wrenches to tighten the nosepiece into and against the end of shaft 125. The nosepiece further includes a tool end 200A coupled to the second end of the body 140.

The tool end 200A includes a channel 205 between its left and right sides that mates with the cylindrical opening 144. The channel 205 allows suture thread in an eyelet of a suture anchor to pass out the sides of the tool end 200A and be routed along sides of the nosepiece toward the install handle.

A pair of opposing flexible arches 203A-203B in the tool end 200A can receive the body of a suture anchor. In this manner the nosepiece can hold a suture anchor for installation by the anchor installation tool.

Referring now to FIG. 2B, a perspective view of a screw-on disposable adjustment tool nosepiece 104B is shown. The nosepiece 104B includes the threaded shaft 135 coupled to one end of its body 140 and a tool end 200B coupled to the opposite end of the body 140. The body 140 includes the opposing jaw receptacles 138A-138B and the rectangular recess 139 to receive various types of wrenches to tighten the nosepiece into and against the end of shaft 125.

The tool end 200B coupled to the second end of the body 140 includes a pair of opposing arches 213A-213B of narrower separation to receive an eyelet of a suture anchor. The tool end 200B may include an opposing pair of beveled surfaces 214A-214B to direct the suture thread up the sides of the nosepiece.

With the pair of opposing arches 213A-213B holding an end of the eyelet of the suture anchor, the eyelet can be turned by the installation tool. With suture thread inserted therein, it is desirable to rotate the eyelet so that the suture thread can be rotated to the desired position.

Referring now to FIG. 2C, a perspective view of a screw-on disposable awl nosepiece 104C is shown. The nosepiece 104C includes the threaded shaft 135 coupled to one end of its body 140 and a tool end 200C coupled to the opposite end of the body 140. The body 140 includes the opposing jaw receptacles 138A-138B and the rectangular recess 139 to receive various types of wrenches to tighten the nosepiece into and against the end of shaft 125.

The tool end 200C includes a solid shaft 223 coupled to the second end of the body 140 that tapers down to a pointed tip 224. The pointed tip 224 of the screw-on disposable awl nosepiece 104C may be used to create a hole into bone or enlarge a hole that was previously drilled into bone by a drill and drill bit.

Assembled Suture Anchor Installation Tool

Figure 3A:
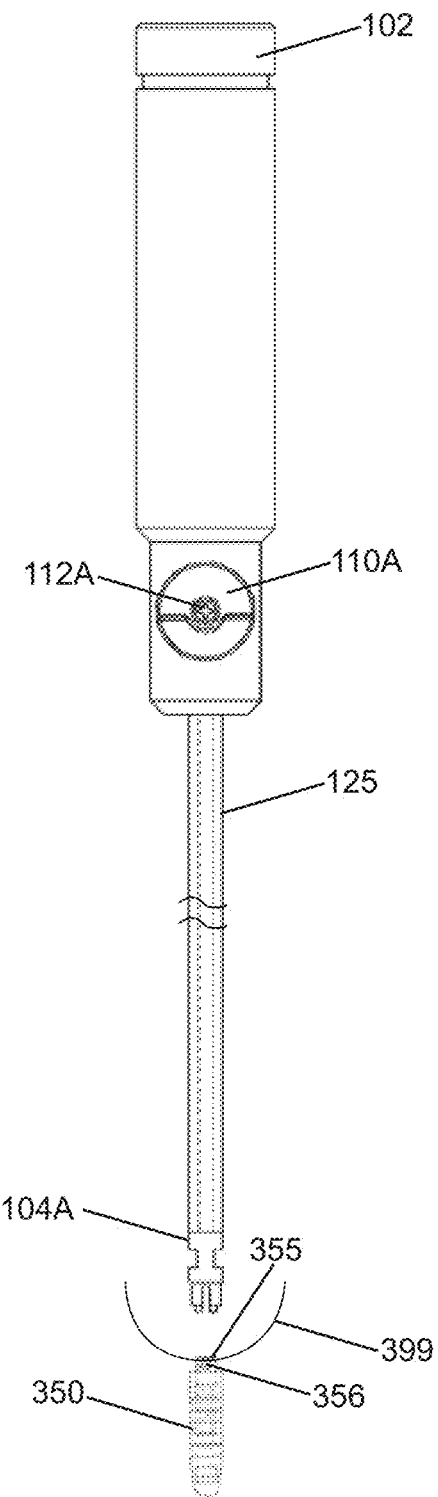
FIG. 3A illustrates a side view of the assembled anchor installation tool with its screw-on disposable tool nosepiece ready to receive a suture anchor and suture thread.
Figure 3B:
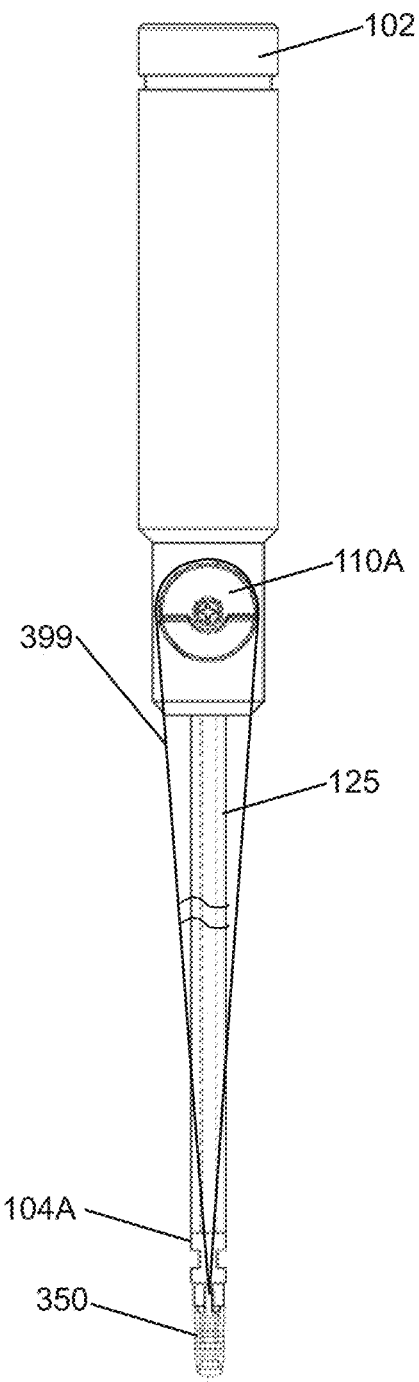
FIG. 3B illustrates a side view of the assembled anchor installation tool with its screw-on disposable tool nosepiece receiving the suture anchor and suture thread.
Figure 3C:
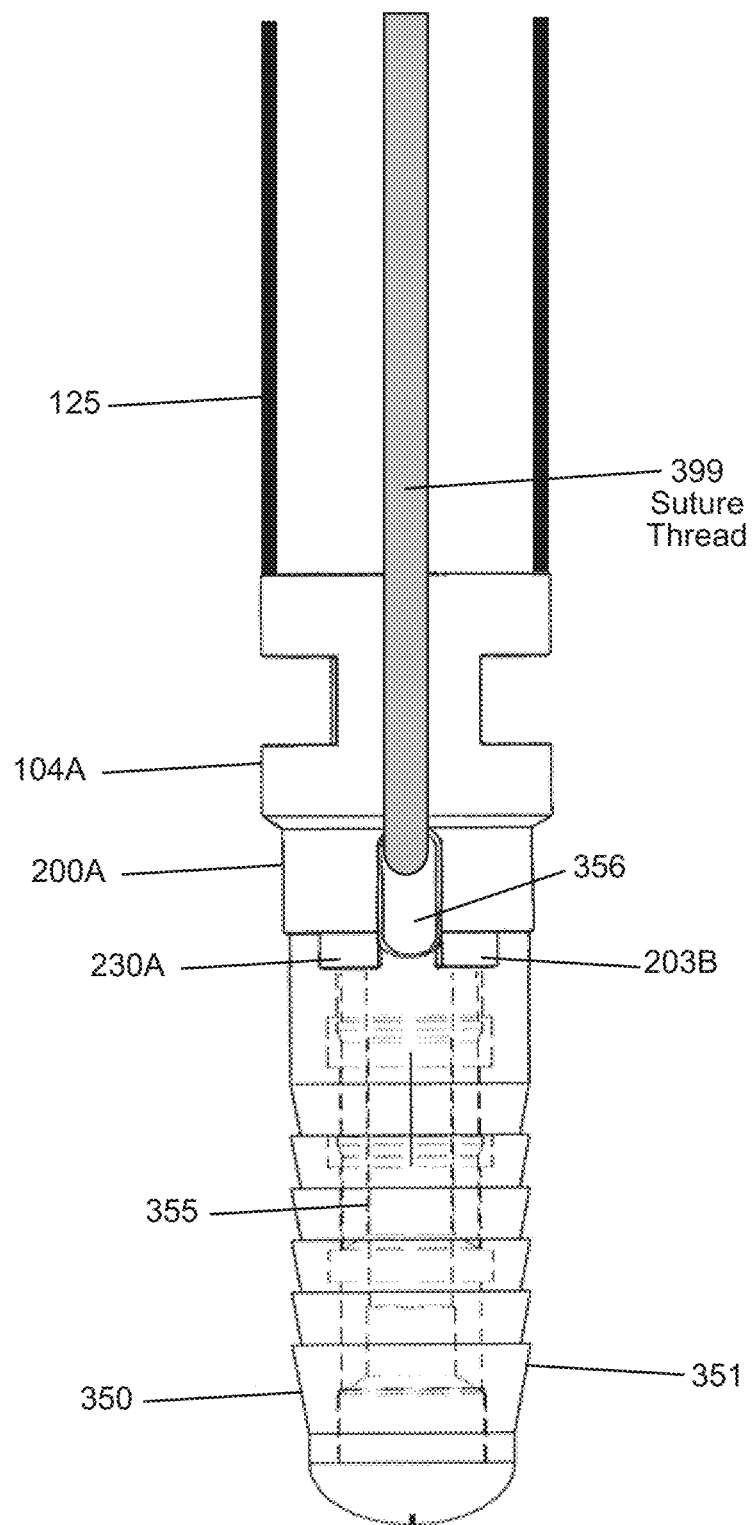
FIG. 3C is a magnified front view of the suture anchor received by the screw-on disposable tool nosepiece of the anchor installation tool.

Reference is now made to FIGS. 3A-3C. In FIG. 3A, a side view of the assembled anchor installation tool is shown. The screw-on disposable anchor install tool nosepiece 104A, the shaft 125, and the install handle 102 are coupled together to form the assembled anchor installation tool. In some embodiments, the suture anchor 350 is coupled to the tool nosepiece 104A as part of the assembled anchor installation tool.

In FIG. 3A, a suture anchor 350 has a suture thread 399 routed through an open eyelet channel 356 of an eyelet pin 355. In an open mode, a portion of the eyelet pin 355 with the eyelet channel 356 extends out from the anchor body 352. The screw-on disposable anchor install tool nosepiece 104A is ready to receive the suture anchor 350 and the suture thread 399.

As better seen in Figure 3C, the suture anchor 350 includes an anchor body 351 coupled to an eyelet pin 355. The eyelet pin 355 includes an eyelet channel 356. The eyelet channel 356 is sized to allow one or more suture threads 399 to route through the eyelet pin. In one embodiment, the end of the eyelet pin 355 is a hexagonal shaped cylinder having openings in opposing faces through which the eyelet channel is routed.

Referring now to FIG. 3B, the suture anchor 350 is mounted to the end of the screw-on disposable anchor install tool nosepiece 104A, which in turn is mounted to the end of the tool 102. Two ends of the suture thread 399 may route along opposing sides of the anchor installation tool to the pair of side cleats 110A-110B. FIG. 3B shows one end of the suture thread 399 wrapped around the side cleat 110A. The side cleats 110A-110B capture the ends of the suture thread 399 against the sides of the body of the install handle. The side cleats 110A-110B can then be rotated to take up slack in the suture thread between the anchor 350 and the cleats.

The suture anchor 350, nosepiece 104A, tool 102, and suture thread 399 can be assembled together and placed in a sterile bag 190 as a kit 100 prior to surgery. A plurality of kits 100 with different dimensions (sizes) and types of suture anchors 350, and other tools with different nosepieces in a plurality of sterile bags 190 may be prepared in advance for surgery on a patient. In this manner, a surgeon has a selection of surgical tools to choose from during a surgery on the patient.

Referring now to FIG. 3C, a magnified side view of the suture anchor 350 received by the screw-on disposable anchor tool nosepiece 104A is shown. The suture thread 399 extends out from the eyelet opening 356 of the eyelet pin 355 and is routed towards a side cleat. The pair of opposing flexible arches 203A-203B in the tool end 200A of the nosepiece 104A receive the eyelet pin 355 and body 351 of the suture anchor 350. The nosepiece 200A holds the suture anchor 350 ready for installation into a hole in a bone by the anchor installation tool.

In some embodiments, the suture anchor 350 and the anchor tool nosepiece 104A are formed together along a separation line between them. For example, the material forming the anchor and nosepiece may be readily breakable. The housing of the suture anchor may formed with the nosepiece and scored along the separation line between each. With the suture anchor 350, nosepiece 104A, and tool 102 coupled together at an one end of the tool 102, the suture anchor 350 can be installed into bone by hammering on the opposite end with a mallet or hammer. After the outer housing of the suture anchor 350 is securely installed into bone of a patient, the tool 102 can be pivoted or wobbled about the separation line in the suture anchor housing to break away the anchor tool nosepiece 104A and tool 102 from the suture anchor 350. The pre-assembled tool with separable suture anchor can speed installation of the suture anchor 350 into bone to reduce the time and costs of surgery.

Disposable/Reusable Components

The suture anchor 350 and suture thread 399 are single use for one patient only. The nosepiece 104 of the installation tool may be for single use or reusable.

The installation handle assembly may in part or fully reused or for single use. In accordance with one embodiment, portions of the handle and shaft of installation tool may be machined out of surgical grade stainless steel (e.g., SST 316 or SST 316L) or aluminum, and some portions may be molded out of plastic, such as the outer handle, the cleats and the knob.

The nosepieces 104A-104C (collectively referred to as nosepieces 104) of the installation tool may be formed out of either surgical grade stainless steel or a plastic/polymer/thermoplastic, such as DELRIN (polyoxymethylene) thermoplastic, to minimize abrasion of sutures. In some cases, the nosepieces (e.g., nosepiece 104A) of the installation tool are formed out of the same material as that of the outer housing of the suture anchor 350.

The handle 102 can be formed out of metal alone for both single or reusable functions. In yet another embodiment, the handle may be made from a combination of plastics and metal, over molded parts, or molded parts to lower its costs for either single use or reuse.

CONCLUSION

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A suture anchor installation system comprising:
   an installation handle including a single cylindrical wall forming a single hollow shaft, the single hollow shaft including a distal end, and a proximal end, a first threaded portion at the distal end, and a second threaded portion at the proximal end;
   a tool nosepiece comprising:
      a body including a first end and a tool end opposite the first end;
      a threaded shaft coupled to the first end of the body and configured to releasably couple to the first threaded portion at the distal end of the single hollow shaft such that the tool nosepiece extends distally from the distal end of the single hollow shaft;
      a cylindrical opening along a longitudinal axis of the body, the threaded shaft, and the tool end to mate with the single hollow shaft;
   a suture anchor configured to couple to the tool end; and
   an eyelet complex impaction rod comprising a single body configured to be inserted into the single hollow shaft of the installation handle and the cylindrical opening of the tool nosepiece, such that the eyelet complex impaction rod is in direct contact with the installation handle, and the eyelet complex impaction rod extending distally from the tool end and having an end to push the suture anchor away from the installation handle and the tool nosepiece.

2. The suture anchor installation system of claim 1, further comprising:
a first sterile bag to receive the installation handle;
a second sterile bag to receive the tool nosepiece;
a third sterile bag to receive the eyelet complex impaction rod; and
a fourth sterile bag to receive the suture anchor.

3. The suture anchor installation system of claim 1, wherein at least the distal end of the eyelet complex impaction rod is cylindrical and includes a circular cross-section.

4. A screw-on disposable anchor install tool nosepiece comprising:
a single body comprising:
a first end including an externally threaded shaft configured to releasably couple to a distal end of a shaft of an installation tool handle;
a tool end opposite the first end including two flexible arches configured to drive a suture anchor, and configured to removably couple to a suture anchor; and
at least three rectangular recessed jaw receptacles between the first end and the tool end to receive one or more wrenches, wherein at least two of the rectangular recessed jaw receptacles are opposing;
wherein the single body, includes a cylindrical opening along a longitudinal axis of the single body from the first end to the tool end.

5. The nosepiece of claim 4, wherein
the tool end includes a channel between a left side and a right side that mates with the cylindrical opening to receive a suture through in an eyelet of the suture anchor.

6. The nosepiece of claim 4, wherein
the two flexible arches are opposing and configured to receive an eyelet of the suture anchor and releasably hold the suture anchor to the shaft of the installation handle for installation into bone.

7. The nosepiece of claim 6, wherein
the body further includes an opposing pair of beveled surfaces to direct a suture thread up the sides of a nosepiece.

8. A suture anchor installation system comprising:
an installation handle comprising a single hollow shaft including a distal end and a proximal end, a first threaded portion at the distal end, and a second threaded portion at the proximal end;
a tool nosepiece comprising:
a body including a first end and a tool end opposite the first end;
wherein the first end of the body includes a threaded shaft and is configured to couple to the distal end of the single hollow shaft such that the tool nosepiece extends distally from the distal end of the single hollow shaft,
a cylindrical opening along a longitudinal axis of the body, the threaded shaft, and the tool end to mate with the single hollow shaft;
a suture anchor configured to couple to the tool end; and
an eyelet complex impaction rod comprising a rod with a rod proximal end and a rod distal end, and a threaded rod handle coupled to the rod proximal end, the rod to be inserted into the single hollow shaft of the installation handle and the cylindrical opening of the tool nosepiece, such that the eyelet complex impaction rod is in direct contact with the installation handle, and the rod distal end extends distally from the tool end and is configured to push the suture anchor away from the installation handle and the tool nosepiece, wherein at least the distal end of the rod is cylindrical and includes a circular cross-section.

\* \* \* \* \*